United States Patent
Lee et al.

(10) Patent No.: US 10,360,443 B2
(45) Date of Patent: Jul. 23, 2019

(54) SYSTEM AND METHOD FOR DETECTING SUBLIMINAL FACIAL RESPONSES IN RESPONSE TO SUBLIMINAL STIMULI

(71) Applicant: NURALOGIX CORPORATION, Toronto (CA)

(72) Inventors: Kang Lee, Toronto (CA); Pu Zheng, Toronto (CA); Marzio Pozzuoli, King (CA)

(73) Assignee: NURALOGIX CORPORATION, Toronto (CA)

(*) Notice: Subject to any disclaimer, the term of this patent is extended or adjusted under 35 U.S.C. 154(b) by 0 days.

(21) Appl. No.: 15/761,891

(22) PCT Filed: Nov. 14, 2017

(86) PCT No.: PCT/CA2017/051355
§ 371 (c)(1),
(2) Date: Mar. 21, 2018

(87) PCT Pub. No.: WO2018/085946
PCT Pub. Date: May 17, 2018

(65) Prior Publication Data
US 2019/0073523 A1 Mar. 7, 2019

Related U.S. Application Data

(60) Provisional application No. 62/421,508, filed on Nov. 14, 2016.

(51) Int. Cl.
*G06K 9/00* (2006.01)
*G06N 20/00* (2019.01)

(52) U.S. Cl.
CPC ..... *G06K 9/00315* (2013.01); *G06K 9/00281* (2013.01); *G06N 20/00* (2019.01)

(58) Field of Classification Search
None
See application file for complete search history.

(56) References Cited

U.S. PATENT DOCUMENTS 8,221,127 B1 * 7/2012 Poulsen ................. G09B 19/00
434/236
9,308,445 B1 * 4/2016 Merzenich ............. A63F 13/80
(Continued)

OTHER PUBLICATIONS

International Search Report corresponding to PCT/CA2017/051355; Canadian Intellectual Property Office, dated Jan. 3, 2018.
(Continued)

*Primary Examiner* — Samah A Beg
(74) *Attorney, Agent, or Firm* — Marc Lampert; Anil Bhole; Bhole IP Law

(57) ABSTRACT

A system and method for detecting subliminal facial responses of a human subject to subliminal stimuli. The method includes: receiving captured first facial response data approximately time-locked with a presentation of subliminal target stimuli to a plurality of human subjects; receiving captured second facial response data approximately time-locked with a presentation of subliminal foil stimuli to the plurality of human subjects; receiving captured unidentified facial response data to a subliminal stimulus from the target human subject; determining a target probability measure that the unidentified facial response data of the target human subject is in response to the subliminal target stimuli using a machine learning model trained with a subliminal response training set, the subliminal response training set comprising the first captured facial response data and the captured second facial response data; and outputting the target probability measure.

20 Claims, 5 Drawing Sheets

(56) References Cited

U.S. PATENT DOCUMENTS

| | | | |
|---|---|---|---|
| 9,503,786 | B2 | 11/2016 | el Kaliouby et al. |
| 9,824,607 | B1* | 11/2017 | Bhattacharyya ......... G06N 5/04 |
| 2009/0018897 | A1* | 1/2009 | Breiter ............... G06Q 30/0203 |
| | | | 705/7.32 |
| 2010/0191124 | A1* | 7/2010 | Prokoski .............. A61B 5/0064 |
| | | | 600/473 |
| 2011/0027764 | A1* | 2/2011 | Bianchi-Demicheli ..................... |
| | | | A61B 5/16 |
| | | | 434/236 |
| 2013/0103624 | A1* | 4/2013 | Thieberger ........... G06Q 10/063 |
| | | | 706/12 |
| 2014/0228701 | A1* | 8/2014 | Chizeck ............. A61B 5/04012 |
| | | | 600/544 |
| 2014/0303991 | A1* | 10/2014 | Frank ................. G06Q 30/0201 |
| | | | 705/2 |
| 2015/0350730 | A1* | 12/2015 | el Kaliouby ........... A61B 5/165 |
| | | | 725/12 |
| 2017/0150907 | A1* | 6/2017 | Duffy ................... A61B 5/1125 |
| 2017/0281067 | A1* | 10/2017 | Hanina .................. A61B 3/032 |
| 2018/0008894 | A1* | 1/2018 | Sack ...................... G06Q 50/10 |

OTHER PUBLICATIONS

Written Opinion of the International Searching Authority corresponding to PCT/CA2017/051355; Canadian Intellectual Property Office; dated Jan. 3, 2018.

Mohan et al., "Effect of subliminal lexical priming on the subjective perception of images: a machine learning approach", PLoS ONE 11(2): e0148332. doi:10.1371/journal.pone.0148332, Published: Feb. 11, 2016 (Nov. 2, 2016), pp. 1-22. URL:<http:Ujoui:nals.plos.org[plosone[article'!id=1 0. 1 371/journal.pone.0 1483 32>.

Lu et al., "Understanding the subliminal affective priming effect of facial stimuli: an ERP study", 1-20 Neuroscience Letters 502 (201 1) 182-185, doi:10.1016/j.neulet.2011.07.040, published in 2011 (2011).

Liu et al., "Unconscious processing of facial emotional valence relation: behavioral evidence of integration between subliminally percieved stimuli", PLoS ONE 11(9): e0I62689. https://doi.org/10.1371/journal.pone.0l62689, Published: Sep. 13, 2016 (Sep. 13, 2006), pp. 1-19, URLI<httpl//j0l1IT.18.1S.pl0S.01'g[plQSOIT16lfl1ltl_CI§2I(If0FIQ. I 37_I/journal.pone.0 1 62689>.

Swinton ct al., "Measuring emotions through a mobile device across borders, ages, genders and more", ESOMAR, Congress 2012, Date of publication: Sep. 13, 2012 (Sep. 13, 2012), pp. 1-12, ISBN: 92-831-0260-6, URL:<https://wwwnffectiva.com/wp-content/uploads/2017/03/Measuring_Emotion_Through_Mobile_E_som_ar,.,pdf>.

Osman et al., "Supervised learning approach to remote heart rate estimation from facial videos", Published in: Automatic Face and Gesture Recognition (FG), 2015 llth IEEE International Conference and Workshops on, Date of Conference: May 4-8, 2015, Date Added to IEEE Xplore: Jul. 23, 2015 (Jul. 23, 2015), pp. 1-6, Electronic ISBN: 978-1-4799-6026-2, INSPEC Accession No. 15309408, DOI: 10.1109fFG.2015.7163150, URL:,<3hhttp:.1£ieexplore.ieee.org/abstract/document/7 163 150/>.

Kodra et al., "From dials to facial coding: Automated detection of spontaneous facial expressions for media research", Published in: Automatic Face and Gesture Recognition (FG), 2013 10th IEEEInternational Conference and Workshops on, Date of Conference: Apr. 22-26, 2013, Date Added to IEEE Xplore: Jul. 15, 2013 (Jul. 15, 2013), Electronic ISBN: 978-1-4673-5546-9, Print ISBN: 978-1-4673-55452, Online ISBN: 978-l-4673-5544-5, INSPEC Accession No. 13653101, DOI: 10.1 109/FG.20 13.655 3780, URL:<http://ieeexploreiee.org >.

Sénéchal et al., "Smile or Smirk! Automatic detection of spontaneous asymmetric smiles to understand viewer experience", Published in: Automatic Face and Gesture Recognition (FG), 2013 10th IEEE International Conference and Workshops on, Date of Conference: Apr. 22-26, 2013, Date Added to IEEE Xplore: Jul. 15, 2013 (Jul. 15, 2013), Electronic ISBN: 978-I-4673-5546-9, Print ISBN: 978-1-4673-5545-2, Online ISBN: 978-1-4673-5544-5, INSPEC Accession No. 13653097, DOI:10. 1109/FG.2013.6553776.

* cited by examiner

SYSTEM AND METHOD FOR DETECTING SUBLIMINAL FACIAL RESPONSES IN RESPONSE TO SUBLIMINAL STIMULI

TECHNICAL FIELD

The following relates generally to detection of human subliminal responses and more specifically to a system and method for detecting subliminal facial responses in response to subliminal stimuli.

BACKGROUND

Humans have a multitude of ways of showing emotions as a response to various stimuli. Some of the stimuli are consciously perceptible, known as above the liminal threshold or at the supraliminal level, and some of the stimuli are not consciously perceptible, known as below the liminal threshold or at the subliminal level.

Further, much of our emotional responses to subliminal stimuli are physically represented in a person's face.

In particular, subliminal response refers to the fact that humans respond to sensory stimuli even when they are presented below the liminal level, under which the stimuli are not consciously perceived. Scientific research on human subliminal responses for nearly a century has well established that subliminal responses are real and robust human responses. Subliminal responses reflect the reactions of the human neural systems that are beyond conscious control. These systems include the autonomous nervous sympathetic and parasympathetic systems, as well as higher subcortical and cortical structures.

Conventionally, subliminal responses have been detected using behavioral techniques, for example measuring response time to stimuli, and/or neuroimaging techniques, for example via electroencephalogram (EEG), galvanic skin response (GSR), functional magnetic resonance imaging (fMRI), event-related potential (ERP), and the like. Conventional approaches of detecting subliminal responses are typically invasive, intrusive, highly expensive and/or requiring of high technical expertise to operate. Accordingly, such techniques are generally only accessible for heavily funded medical and research purposes, but are not available for wide everyday usage including practical applications, for example, market analytics.

Some conventional techniques for detecting emotion, such as computer vision, rely exclusively on facial expression and are ineffective for detecting subliminal responses. Unlike facial-expression-based methods, physiological-information-based methods may be able to detect some subliminal emotional responses. Typically, researchers detect such physiological signals by attaching sensors to the face or body. Polygraphs, electromyography (EMG) and electroencephalogram (EEG) are examples of such technologies, and are highly technical, invasive, and/or expensive. They are also subjective to motion artifacts and manipulations by the subject.

Detecting emotional responses based on imaging techniques, such as fMRI, do not require attaching sensors to the body. However, such techniques are prohibitively expensive and susceptible to motion artifacts that can lead to unreliable readings. Alternatively, hyperspectral imaging may be employed to capture increases or decreases in cardiac output or "blood flow" which may then be correlated to emotional states. The disadvantages present with the use of hyperspectral images include cost and complexity in terms of storage and processing.

Other conventional approaches are concerned with using subliminal presentations to change a subject's behavior or control a subject's mind. Such conventional approaches are concerned with what subjects will do behaviorally when being exposed to subliminal messages, rather than measuring subliminal responses of the subjects to subliminal stimuli.

SUMMARY

In an aspect, there is provided a computer-implemented method for detecting subliminal facial responses of a target human subject to subliminal stimuli, the method comprising: receiving captured first facial response data approximately time-locked with a presentation of subliminal target stimuli to a plurality of human subjects; receiving captured second facial response data approximately time-locked with a presentation of subliminal foil stimuli to the plurality of human subjects; receiving captured unidentified facial response data to a subliminal stimulus from the target human subject; determining a target probability measure that the unidentified facial response data of the target human subject is in response to the subliminal target stimuli using a machine learning model trained with a subliminal response training set, the subliminal response training set comprising the first captured facial response data and the captured second facial response data; and outputting the target probability measure.

In a particular case, the method further comprising determining a foil probability measure that the unidentified facial response data of the target human subject is in response to the subliminal foil stimuli, and outputting the foil probability measure.

In another case, the method further comprising determining an intensity measure for the unidentified facial response data of the target human subject in response to the subliminal target stimuli, and outputting the intensity measure.

In yet another case, the subliminal target stimuli and the subliminal foil stimuli comprise visual stimuli.

In yet another case, the subliminal target stimuli and the subliminal foil stimuli comprise auditory stimuli.

In yet another case, the subliminal target stimuli and the subliminal foil stimuli are presented for less than approximately one second.

In yet another case, the subliminal target stimuli and the subliminal foil stimuli are presented for less than approximately twenty milliseconds.

In yet another case, the first facial response data, the second facial response data, and the unidentified facial response data are captured from predetermined regions of interest (ROIs) on the face of the subject, and the response data is averaged for each of the ROIs.

In yet another case, the first facial response data, the second facial response data, and the unidentified facial response data each comprise at least one of transdermal optical imaging data, facial expression data, thermal imaging data, and eye tracking data.

In yet another case, the transdermal optical imaging data is acquired by determining, using a machine learning model trained with a hemoglobin concentration (HC) training set, bit values from a set of bitplanes in a captured image sequence that represent the HC changes of the human subject, the set of bitplanes being those that are determined to approximately maximize a signal-to-noise ratio (SNR), the HC training set comprising bit values from each bitplane of images captured from a set of subjects for which HC is known.

In an aspect, there is provided a system for detecting subliminal facial responses of a target human subject to subliminal stimuli, the system comprising one or more processors and a data storage device, the one or more processors configured to execute: a facial response module to receive captured first facial response data from an input sensing device approximately time-locked with a presentation of subliminal target stimuli by a stimuli device to a plurality of human subjects, the facial response module further receives captured second facial response data from the input sensing device approximately time-locked with a presentation of subliminal foil stimuli by the stimuli device to the plurality of human subjects; the facial response module further receives captured unidentified facial response data from the input sensing device to a subliminal stimulus presented by the stimuli device from the target human subject; a machine learning module to determine a target probability measure that the unidentified facial response data of the target human subject is in response to the subliminal target stimuli using a machine learning model trained with a subliminal response training set, the subliminal response training set comprising the first captured facial response data and the captured second facial response data; and an output module to output the target probability measure.

In a particular case, the machine learning module further determines a foil probability measure that the unidentified facial response data of the target human subject is in response to the subliminal foil stimuli, and the output module outputs the foil probability measure.

In another case, the machine learning module further determines an intensity measure for the unidentified facial response data of the target human subject in response to the subliminal target stimuli, and the output module outputs the intensity measure.

In yet another case, the stimuli device presents the subliminal target stimuli and the subliminal foil stimuli as visual stimuli.

In yet another case, the stimuli device presents the subliminal target stimuli and the subliminal foil stimuli as auditory stimuli.

In yet another case, the stimuli device presents the subliminal target stimuli and the subliminal foil stimuli for less than approximately one second.

In yet another case, the stimuli device presents the subliminal target stimuli and the subliminal foil stimuli for less than approximately twenty milliseconds.

In yet another case, the first facial response data, the second facial response data, and the unidentified facial response data are captured by the input sensing device from predetermined regions of interest (ROIs) on the face of the subject, and the facial response module or the machine learning module averages the response data for each of the ROIs.

In yet another case, the first facial response data, the second facial response data, and the unidentified facial response data each comprise at least one of transdermal optical imaging data, facial expression data, thermal imaging data, and eye tracking data.

In yet another case, the transdermal optical imaging data is acquired by determining, using a machine learning model trained with a hemoglobin concentration (HC) training set, bit values from a set of bitplanes in a captured image sequence that represent the HC changes of the human subject, the set of bitplanes being those that are determined to approximately maximize a signal-to-noise ratio (SNR), the HC training set comprising bit values from each bitplane of images captured from a set of subjects for which HC is known.

These and other aspects are contemplated and described herein. It will be appreciated that the foregoing summary sets out representative aspects of systems and methods for detecting subliminal facial responses in response to subliminal stimuli to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
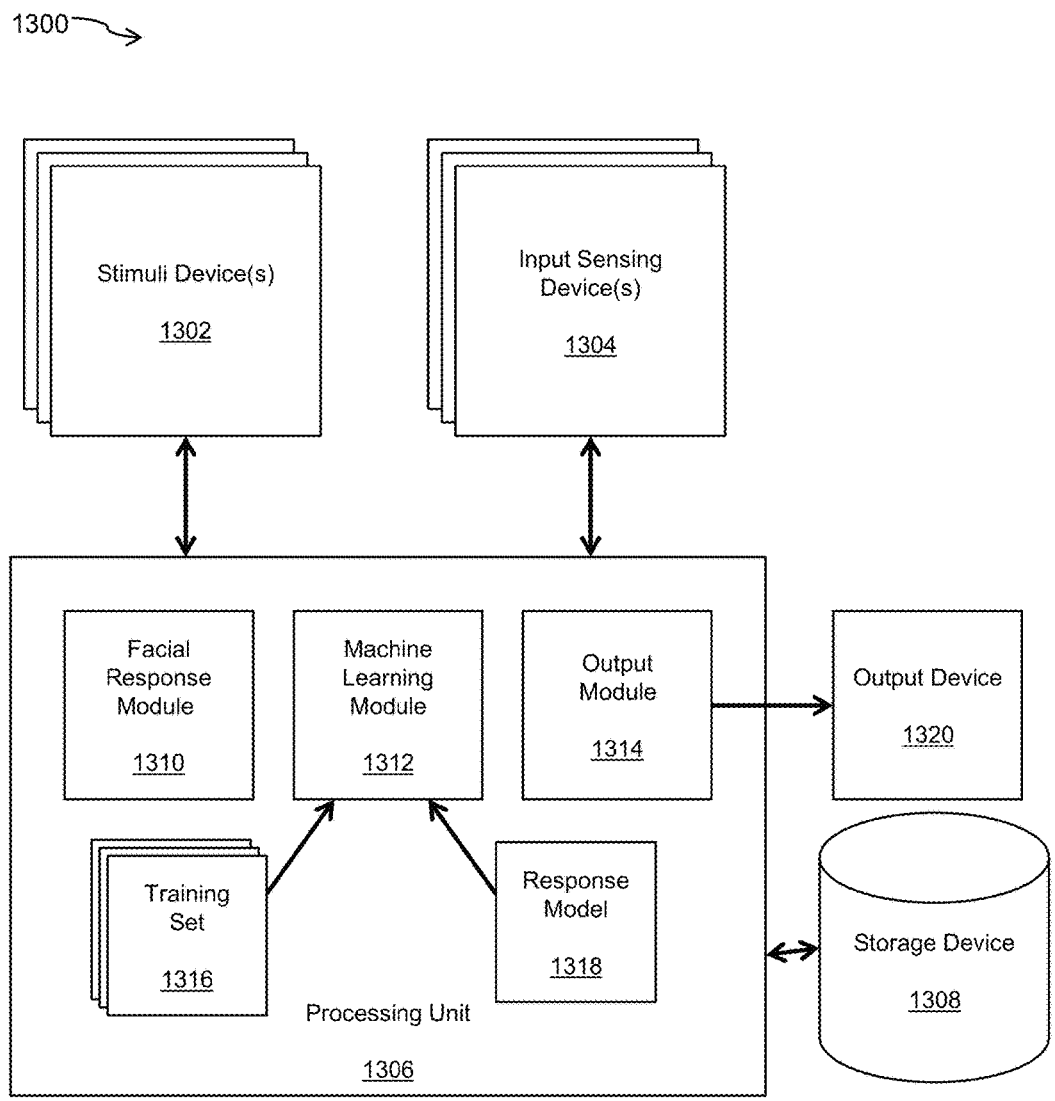
FIG. 1 is an block diagram of a system for detecting subliminal facial responses to subliminal stimuli, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to detection of human subliminal responses and more specifically to a system and method for detecting subliminal facial responses to subliminal stimuli.

In embodiments of the system and method described herein, technical approaches are provided to solve the technological problem of detecting a human's subliminal responses based on examining their facial responses to subliminal stimuli using a remote, touchless, non-invasive, and non-intrusive system. In some cases, the approaches can potentially be accomplished covertly. This approach capitalizes on the fact that human faces are highly responsive to various stimuli, including visual and auditory stimuli (subliminal or supraliminal), and subliminal and supraliminal facial responses can be measured remotely and non-invasively using optical imaging techniques.

Turning to FIG. 1, a system for detecting subliminal facial responses 1300 is shown. The system 1300 includes one or more stimuli devices 1302, one or more input sensing devices 1304, a processing unit 1306, a storage device 1308, and an output device 1320. The processing unit 1306 includes a facial response module 1310, a machine learning module 1312, which includes a training set 1316 and a computation response model 1318, and an output module 1314. The storage device 1308 communicating with the processing unit 1306 provides a repository of data. The output device 1320 can be any device suitable for providing the information outputted by the output module; for example, a computer monitor or a tablet display.

In an exemplary embodiment, the system 1300 presents human subjects with target subliminal sensory stimuli via the one or more stimuli devices 1302. The stimuli may be visual, audio or other sensory stimuli. The stimuli device 1302 producing the visual stimuli can be, for example, a computer monitor or a light display. The visual stimuli are, in this example, presented transitorily via the stimuli device 1302. As an example, the visual stimuli can last less than approximately a second, and preferably, less than approximately 20 milliseconds. The target visual stimuli can be flanked by a pre-stimulus visual mask, for example a noise pattern, and a post-stimulus visual mask, for example the same noise pattern or a different noise pattern. The pre-stimulus masks are used to block the sensory system from detecting the presence of the subliminal stimulus and sending the information to the supraliminal level. The post-stimulus masks are used to "erase" any traces of the subliminal stimuli in the sensory system. The visual masks are typically above the liminal level, i.e., at the supraliminal level. In some cases, the target visual stimuli can be presented to the human subject, interspersed with the visual masks, more than once.

In order to ensure specificity of the target stimuli responses, the human subjects can also be presented with foil subliminal visual stimuli via the stimuli device 1302. The foil visual stimuli, in this example, are also presented transitorily, for example lasting less than a second, or preferably, less than approximately 20 milliseconds, via the stimuli device 1302. These foil visual stimuli are similar to the target stimuli in all aspects except for their information content. As an example, the target subliminal stimuli may include faces known to the human subject and the foil visual stimuli may be faces that are unknown to the human subject.

In other embodiments, the stimuli device 1302 can present subliminal target auditory stimuli to the human subject. The stimuli device 1302 can be, for example, speakers or headphones. The target auditory stimuli, in this example, are presented transitorily, for example lasting approximately 20 milliseconds, via the stimuli device 1302. The target auditory stimuli can be flanked by supraliminal audio masks before and after the target auditory stimuli. In some cases, the target audio stimuli can be presented to the human subject, along with the audio masks, more than once.

To ensure specificity of the target-related responses, the stimuli device 1302 can also present the same human subjects with foil subliminal auditory stimuli also flanked by supraliminal auditory stimuli. The foil auditory stimuli are similar to the target auditory stimuli in all aspects except for their information content. For example, the target auditory stimuli might be the name of a person known to the human subject, while the foil subliminal stimuli might be the name of a person unknown to the human subject.

In further embodiments, the stimuli device 1302 can include a combination of auditory and visual subliminal stimuli. In yet further embodiments, the stimuli device 1302 can include other types of stimulation to the human subject in the form of other sensory and perceptual modalities; for example, tactile stimuli.

During the presentation of the target stimuli and the foil stimuli to the human subject by the stimuli device 1302, the facial responses, time-locked with the onset and duration of the target stimuli and foil stimuli, are captured by the input sensing device 1304. In an embodiment, the input sensing device 1304 includes a conventional digital video camera 205. The digital video camera 205 is used to capture the transdermal blood flow response using the transdermal optical imaging approach described herein. In further embodiments, the digital video camera 205 can be used to capture facial expressions (or microexpressions) of the human subject. In yet further embodiments, the input sensing device 1304 can include a thermal video camera to capture facial thermal responses of the human subject. In yet further embodiments, the input sensing device 1304 can include an infra-red camera to capture information regarding eye movements and/or pupillary dilations of the human subject.

In some cases, and particularly with respect to transdermal facial blood flow, the human subject's face can be divided into multiple regions of interests; for example, forehead, nose, cheek, and the like. The regions of interest can be manually or automatically selected.

In a further embodiment, the input sensing device 1304 will include combinations of input devices, for example, capturing data related to two or more of the transdermal optical imaging (TOI), the thermal imaging, the eye tracking, and the facial expression (or microexpression). In this case, the captured data will be multi-dimensional given that the data is captured from multiple regions of the human subject's face. As an example, the facial expression and transdermal optical imaging approaches can be done simultaneously because both use optical digital cameras 205. The thermal imaging can be also included, for example, if the digital camera 205 includes a thermal imaging component. As well, the eye tracking can also be included, for example, if there is infrared light source emitting from or adjacent the digital camera 205.

As an example of multi-dimensional captured input data, transdermal facial blood flow data can be obtained using the TOI technique. It will be appreciated that the other above-mentioned techniques may alternatively or additionally be utilized. Using TOI, the input sensing device 1304 can capture facial blood flow data from a set of regions of interests (ROIs) on the face of the human subject. Regions of interest can include, for example, the forehead, nose, left and right cheeks, chin, and the like. Data from each of the regions of interest will be temporal sequences of facial blood flow changes in that particular region of interest. In the case of facial thermal response data, multi-dimensional captured input data will also be from different areas of interests; for example, the forehead, nose, eye lids, and the like. In the case of multi-dimensional facial expression data, the input sensing device 1304 can capture facial expressions in different emotional states and types; for example, in joy, anger, sadness, and the like. Data for each facial emotion type can include data representing moment by moment changes of intensity, or a probability of that particular emotion. In the case of multi-dimensional eye tracking data, the input sensing device 1304 can capture at least one of the changes in the directions of the eye movements, the speed of the eye movements, the pupillary dilations of the right and left eyes at each point in time. Emotion probability may be determined using a suitable statistical analysis utilizing a training set of labeled data.

The transdermal optical imaging technique, as captured by the input sensing device 1304, uses that fact that the sympathetic and parasympathetic nervous systems have changes in blood flow resulting from responses to various stimuli. It has been found that an individual's blood flow is controlled by the sympathetic and parasympathetic nervous system, which is beyond the conscious control of the vast majority of individuals. Thus, an individual's internally experienced response can be readily detected by monitoring their blood flow. Internal systems prepare humans to cope with different situations in the environment, including those as a result of stimuli, by adjusting the activations of the autonomic nervous system (ANS). Basic stimuli responses have distinct ANS signatures. Blood flow in most parts of the face such as eyelids, cheeks and chin is predominantly controlled by the sympathetic vasodilator neurons, whereas blood flowing in the nose and ears is mainly controlled by the sympathetic vasoconstrictor neurons; in contrast, the blood flow in the forehead region is innervated by both sympathetic and parasympathetic vasodilators. Thus, different internal response states have differential spatial and temporal activation patterns on the different parts of the face. By obtaining hemoglobin data from the system, facial hemoglobin concentration (HC) changes in various specific facial areas may be extracted.

The blood flow data signal is specified by the interpretation of the HC changes. As an example, the system 100 can monitor stationary HC changes contained by a selected ROI over time, by observing (or graphing) the resulting temporal profile (for example, shape) of the selected ROI HC intensity values over time. In some cases, the system 100 can monitor more complex migrating HC changes across multiple ROIs by observing (or graphing) the spatial dispersion (HC distribution between ROIs) as it evolves over time.

Figure 4:
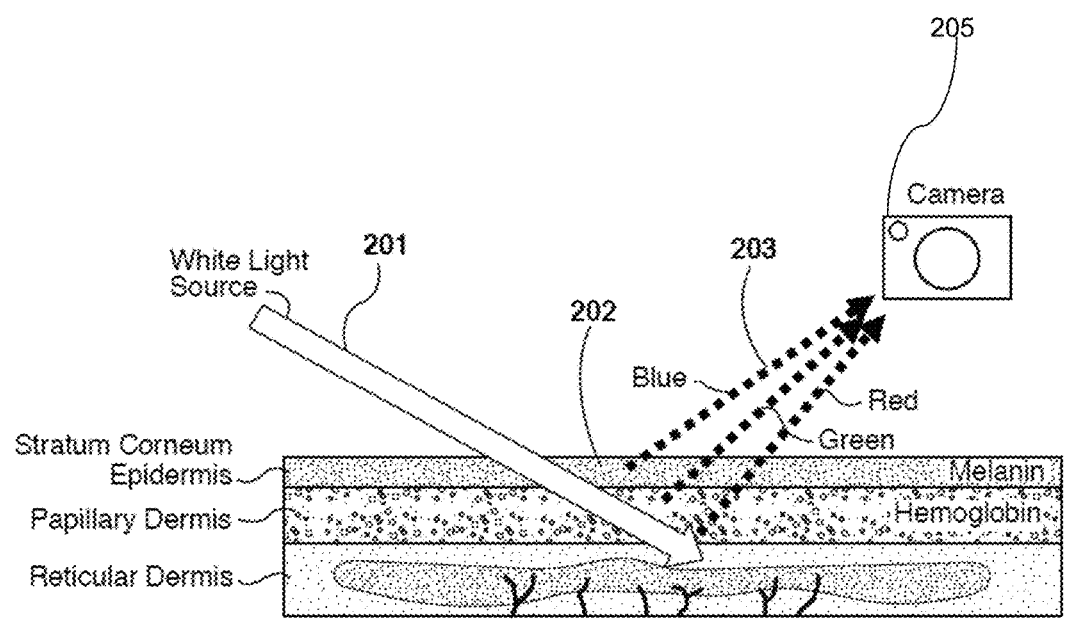
FIG. 4 illustrates re-emission of light from skin epidermal and subdermal layers.
Figure 5:
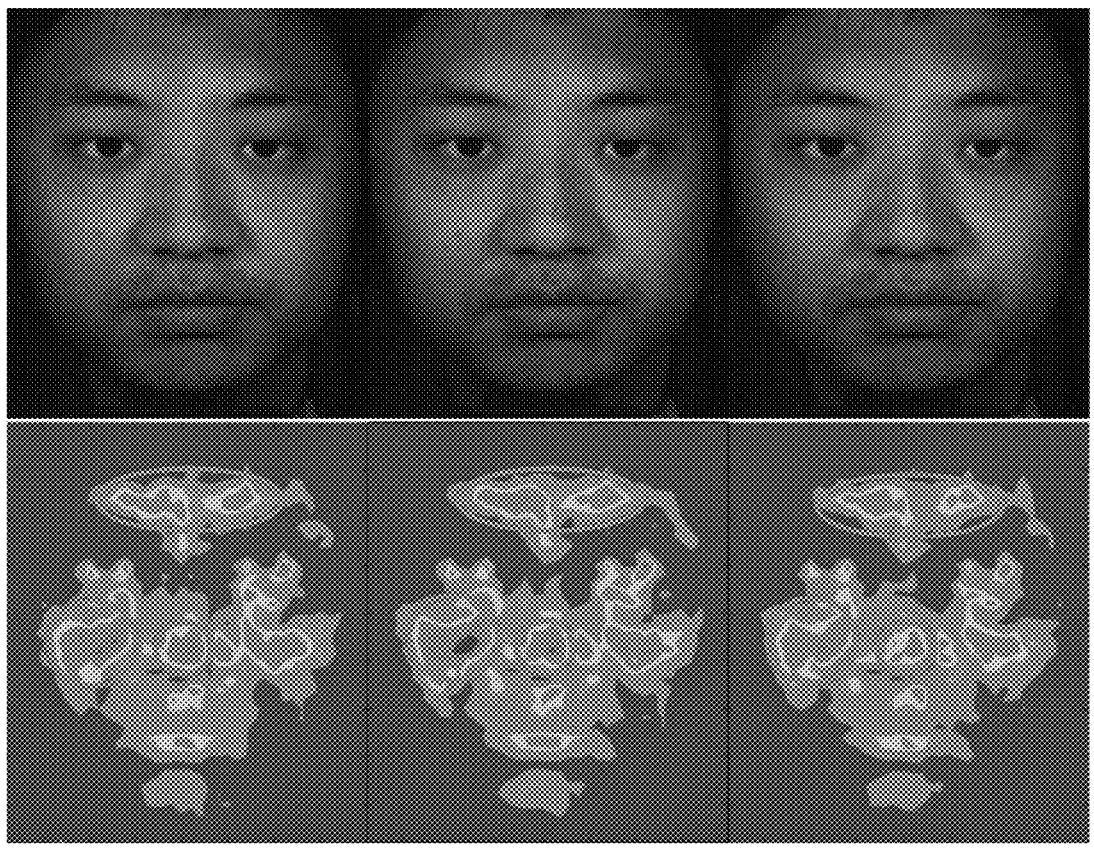
FIG. 5 is a set of surface and corresponding transdermal images illustrating change in hemoglobin concentration for a particular human subject at a particular point in time.

It has been found that it is possible to isolate hemoglobin concentration (HC) from raw images taken from a traditional digital camera 205. Referring now to FIG. 4, a diagram illustrating the re-emission of light from skin is shown. Light 201 travels beneath the skin 202, and re-emits 203 after travelling through different skin tissues. The re-emitted light 203 may then be captured by optical cameras 205. The dominant chromophores affecting the re-emitted light are melanin and hemoglobin. Since melanin and hemoglobin have different color signatures, it has been found that it is possible to obtain images mainly reflecting HC under the epidermis as shown in FIG. 5.

In a particular case, isolating HC can be accomplished by analyzing bitplanes in the sequence of video images received from the camera 205 to determine and isolate a set of the bitplanes that approximately maximize signal to noise ratio (SNR). The determination of high SNR bitplanes is made with reference to an HC training set of images constituting the captured video sequence, in some cases, supplied along with other devices, for example, EKG, pneumatic respiration, blood pressure, laser Doppler data collected from the human subjects in order to provide ground truth to train the training set.

Bitplanes are a fundamental aspect of digital images. Typically, a digital image consists of certain number of pixels (for example, a width×height of 1920×1080 pixels). Each pixel of the digital image having one or more channels (for example, color channels red, green, and blue (RGB)). Each channel having a dynamic range, typically 8 bits per pixel per channel, but occasionally 10 bits per pixel per channel for high dynamic range images. Whereby, an array of such bits makes up what is known as the bitplane. In an example, for each image of color videos, there can be three channels (for example, red, green, and blue (RGB)) with 8 bits per channel. Thus, for each pixel of a color image, there are typically 24 layers with 1 bit per layer. A bitplane in such a case is a view of a single 1-bit map of a particular layer of the image across all pixels. For this type of color image, there are therefore typically 24 bitplanes (i.e., a 1-bit image per plane). Hence, for a 1-second color video with 30 frames per second, there are at least 720 (30×24) bitplanes. In the embodiments described herein, Applicant recognized the advantages of using bit values for the bitplanes rather than using, for example, merely the averaged values for each channel. Thus, a greater level of accuracy can be achieved for making predictions of HC changes, and as described for making predictions, because employing bitplanes provides a greater data basis for training the machine learning model.

The raw signals can be pre-processed using one or more filters, depending on the signal characteristics. Such filters may include, for example, a Butterworth filter, a Chebycheff filter, or the like. Using the filtered signals from two or more ROIs, machine learning is employed to systematically identify bitplanes that will significantly increase the signal differentiation (for example, where the SNR improvement is greater than 0.1 db) and bitplanes that will contribute nothing or decrease the signal differentiation. After discarding the latter, the remaining bitplane images can optimally determine the bold flow.

The machine learning process involves manipulating the bitplane vectors (for example, 24 bitplanes×60 hz) using the bit value in each pixel of each bitplane along the temporal dimension. In one embodiment, this process requires subtraction and addition of each bitplane to maximize the signal differences in all ROIs over the time period. In some cases, to obtain reliable and robust computational models, the entire dataset can be divided into three sets: the training set (for example, 80% of the whole subject data), the test set (for example, 10% of the whole subject data), and the external validation set (for example, 10% of the whole subject data). The time period can vary depending on the length of the raw data (for example, 15 seconds, 60 seconds, or 120 seconds). The addition or subtraction is performed in a pixel-wise manner. An existing machine learning algorithm, the Long Short Term Memory (LSTM) neural network, or a suitable alternative thereto is used to efficiently and obtain information about the improvement of differentiation in terms of accuracy, which bitplane(s) contributes the best information, and which does not in terms of feature selection. The Long Short Term Memory (LSTM) neural network allow us to perform group feature selections and classifications. The LSTM machine learning algorithm are discussed in more detail below. From this process, the set of bitplanes to be isolated from image sequences to reflect temporal changes in HC is obtained.

The data captured by the one or more input sensing devices 1304 are sent to the facial response module 1310 for processing by the processing unit 1306. In some cases, the facial response module 1310 can instead be integral to the input sensing device 1304.

The captured data received by the facial response module 1310, representing the human subject's facial responses towards the target and foil subliminal stimuli, can be analyzed by the machine learning module 1312 using machine learning approaches. The machine learning module 1312, either supervised or unsupervised, aims to use the captured data to optimally differentiate a pattern of subliminal facial responses towards the target subliminal stimuli from a pattern of subliminal facial responses towards the foil subliminal stimuli. The machine learning module 1312 also can develop computational response models 1318 to characterize the subliminal responses of the human subject towards the target subliminal stimuli versus the subliminal responses of the human subject towards the foil subliminal stimuli. In this case, the captured data represents the training set 1316, upon which the machine learning module 1312 uses to refine the response model 1318.

A number of machine learning approaches can be used by the machine learning module 1312. For example, the Long Short Term Memory (LSTM) neural network, GPNet, or a suitable alternative thereto, can be used by the machine learning module 1312 to efficiently improve the accuracy of differentiation between responses to target subliminal stimuli and foil subliminal stimuli. As described herein, the Long Short Term Memory (LSTM) neural network allows the machine learning module 1312 to perform group feature selections and classifications.

Using the training sets 1316 of subliminal data, machine learning approaches by the machine learning module 1312 can employed to build computational models for responses to target stimuli and responses to foil stimuli. The response models 1318 are created using data relating to a training group of human subjects; preferably those subjects include a new multi-ethnic group of training subjects with different skin types, gender, age, and the like. The training set 1316 includes facial responses for the training subjects when those subjects were exposed to subliminal target stimuli and subliminal foil stimuli. As an example, a set of visual stimuli are pictures of a familiar person as target subliminal stimuli and pictures of unknown person as foil subliminal stimuli. In further examples, the stimuli could include subliminally presented sounds, auditory-visual combinations, or other sensory and/or perceptual modalities.

In an exemplary embodiment, the machine learning module 1312 uses a machine learning approach that involves a portion of the captured response data (for example, 70%, 80%, or 90% of the captured response data) and uses the remaining captured response data to validate the machine learning model.

The machine learning module 1312 can build response models 1318 to differentiate between subliminal responses to targets and foils. To build the response model 1318, the machine learning module 1312 intakes the captured data of facial responses from multiple human subjects. The captured data, representing the training set 1316, are extracted as a function of time for the point in time when the human subject was presented with a particular subliminal stimulus. In some cases, to increase a signal to noise ratio (SNR), for example in thermal imaging or transdermal optical imaging, the human subject's face can be divided into a plurality of regions of interest (ROI), preferably divided according to their differential underlying autonomic nervous system (ANS) regulatory mechanisms. The ROIs can be automatically detected with the use of a face tracking software. The machine learning module 1312 can then average the data in each ROI. This information can then form the basis for the training set 1316.

Once the machine learning module 1312 has developed the response model 1318, the machine learning module 1312 can capture unidentified facial response data to a stimulus of any human subject and apply the captured data to the response model 1318. With application to the response model 1318, the machine learning module 1312 can identify whether the human subject's subliminal response, as captured by the one or more input sensing devices 1304, is to subliminal target stimuli or foil stimuli. The output module 1314 can then utilize the information from the machine learning module 1312 and output (1) an estimated statistical probability that the human subject's subliminal response state belongs to either subliminal target stimuli or foil stimuli, and/or (2) a normalized intensity measure of such response. Normalized intensity can be determined, using all subjects' data, by suitable statistical methods to compute the means and standardization of their facial subliminal response levels to a particular subliminal stimulus and then use these parameters to produce z-scores for each subject that index his or her response intensity towards a particular subliminal stimulus. Z-scores can be determined, for example, using:

$$Z = (\text{raw score} - \text{mean})/\text{standard deviation}.$$

In some cases, where there are long-running stimuli device(s) 1302, such as long-running video streams, and where subliminal states of the human subject change and intensity fluctuates over time, then the output module 1314 can change the probability estimation and intensity scores over time. Such changes can rely on the subliminal response data based on a moving time window, for example 10, 15 or 20 seconds. It will be appreciated that in these cases, the confidence level of categorization (subliminal target stimuli versus foil stimuli) may be less than 100%.

In some embodiments, the machine learning module 1312 may use a Long Short Term Memory (LSTM) neural network architecture, which is a category of neural network model specified for sequential data analysis and prediction.

The LSTM neural network comprises at least three layers of cells. The first layer is an input layer, which accepts the input data. The second (and perhaps additional) layer is a hidden layer, which is composed of memory cells 1400 (illustrated in FIG. 2). The final layer is output layer, which generates the output value based on the hidden layer using Logistic Regression.

Figure 2:
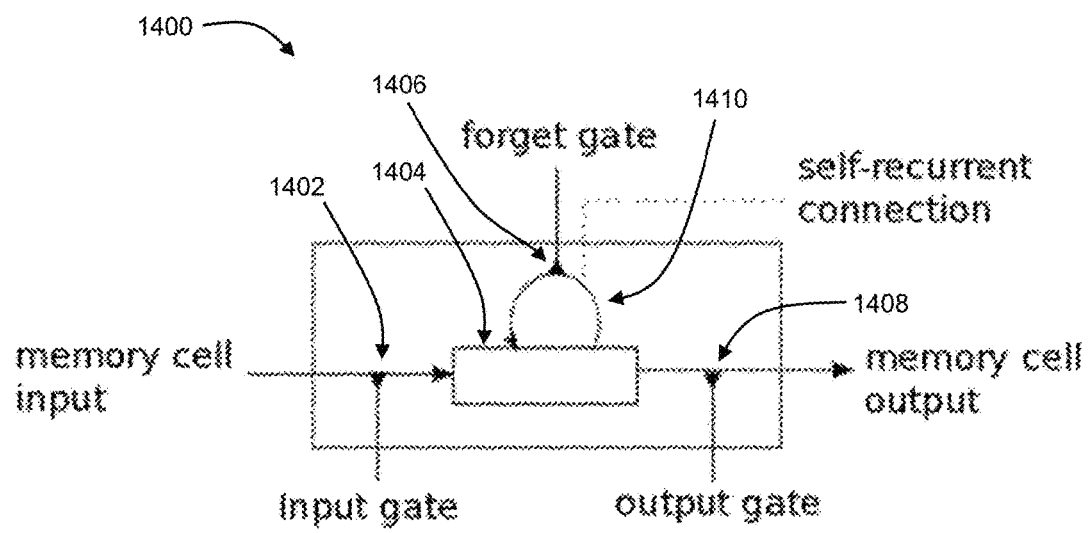
FIG. 2 is a diagrammatic representation of a memory cell.

Each memory cell 1400, as illustrated in FIG. 2, includes an input gate 1402, a neuron 1404 with a self-recurrent connection (a connection to itself) 1410, a forget gate 1406 and an output gate 1408. The self-recurrent connection 1410 can have a weight of 1.0, which ensures that, barring any outside interference, the state of a memory cell can remain constant from one time step to another. The gates serve to modulate the interactions between the memory cell itself and its environment. The input gate 1402 permits or prevents an incoming signal to alter the state of the memory cell 1400. On the other hand, the output gate 1408 can permit or prevent the state of the memory cell from having an effect on other memory cells that are in communication with the subject memory cell 1400. As well, the forget gate 1406 can modulate the memory cell's self-recurrent connection 1410, permitting the cell 1400 to remember or forget its previous state, as needed.

The equations below describe how a layer of memory cells is updated at every time step t. In these equations:
$x_t$ is the input array to the memory cell layer at time t. In our application, this is the blood flow signal at all ROIs $$\vec{x}_s = [x_{1t}, x_{2t}, \ldots, x_{nt}]$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{C}_t$ the candidate value for the states of the memory cells at time t:

$$i_t = \sigma(W_i x_t + U_i h_{t-1} + b_i)$$

$$\tilde{C}_t = \tan h(W_c x_t + U_c h_{t-1} + b_c)$$

Second, we compute the value for $f_t$, the activation of the memory cells' forget gates at time t:

$$f_t = \sigma(W_f x_t + U_f h_{t-1} + b_f)$$

Given the value of the input gate activation $i_t$, the forget gate activation $f_t$ and the candidate state value $\tilde{C}_t$, we can compute $C_t$ the memory cells' new state at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tan h(C_t)$$

Based on the model of memory cells, for the blood flow distribution at each time step, we can calculate the output from memory cells. Thus, from an input sequence $x_0, x_1, x_2, \ldots, x_n$, the memory cells in the LSTM layer will produce a representation sequence $h_0, h_1, h_2, \ldots, h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \mathrm{softmax}(W_{output} h_t + b_{output})$$

where $W_{output}$ is the weight matrix from the hidden layer to the output layer, and $b_{output}$ is the bias vector of the output layer. The condition with the maximum accumulated probability will be the predicted condition of this sequence.

Figure 3:
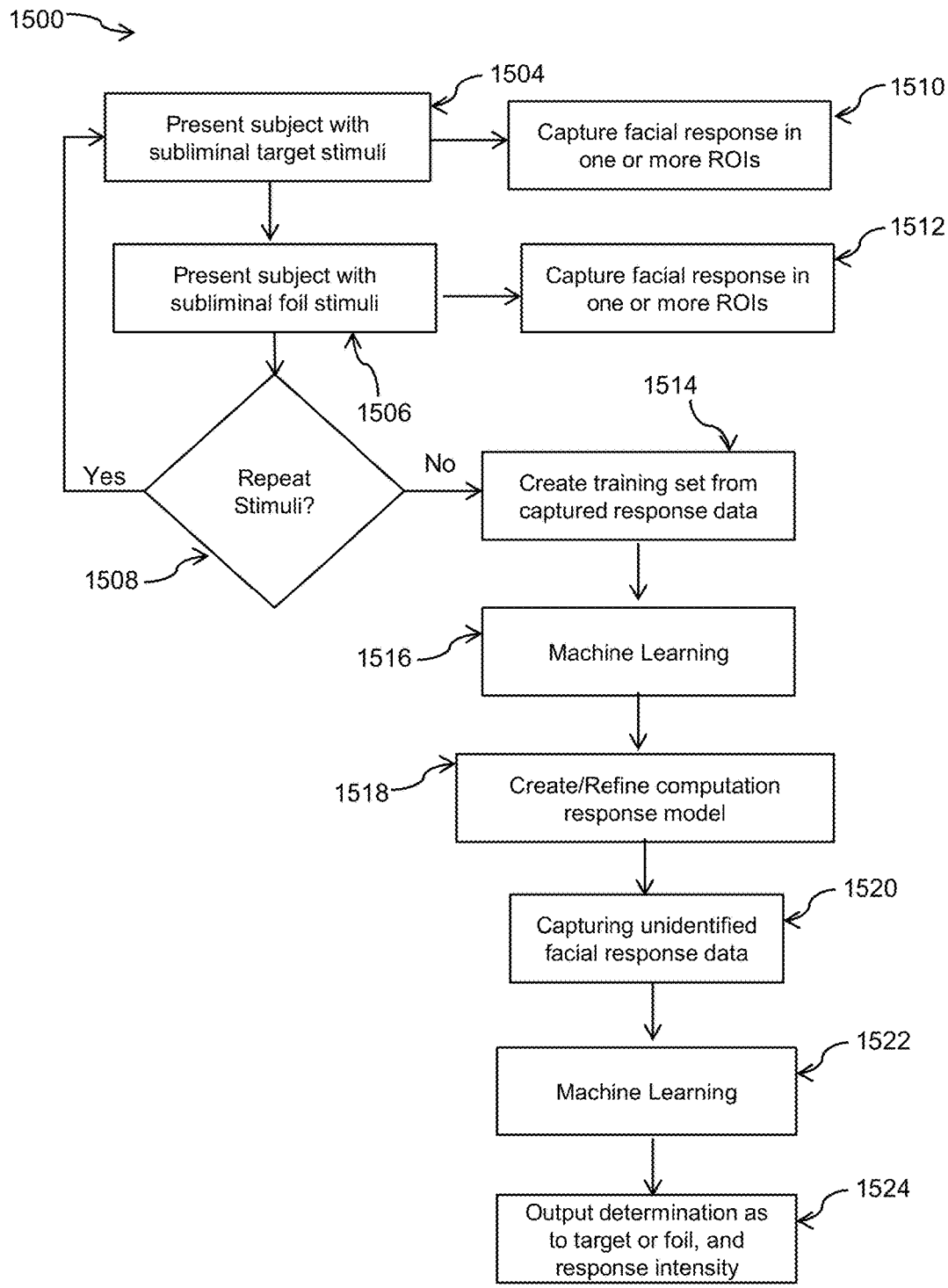
FIG. 3 is a flowchart for a method for detecting subliminal facial responses to subliminal stimuli, according to an embodiment.

Turning to FIG. 3, a flowchart Is shown for a method 1500 for creating a training set of subliminal facial response and a model for determining subliminal responses.

At block 1504, the one or more stimuli devices 1302 present the human subject with target stimuli for which it is known with suitable confidence the human subject will respond in a particular way (i.e., in such a way that the observed response can be labeled). Each of the subliminal target stimuli may be flanked by a pre-stimulus mask and/or a post-stimulus mask. While the stimuli device 1302 presents the target stimuli, at block 1510, the one or more input sensing devices 1304 capture facial response data, approximately time-locked to the presentation of the subliminal target stimuli (i.e., response data received while the subliminal target stimuli is presented to the subject).

At block 1506, the one or more stimuli devices 1302 present the human subject with subliminal foil stimuli. Each of the subliminal foil stimuli may be flanked by a pre-stimulus mask and/or a post-stimulus mask. While the stimuli device 1302 presents the subliminal foil stimuli, at block 1512, the one or more input sensing devices 1304 capture facial response data, approximately time-locked to the presentation of the subliminal foil stimuli (i.e., response data received while the subliminal foil stimuli is presented to the subject).

At block 1508, the facial response module 1310 determines if more captured response data is required. If more captured response data is required, the stimuli device 1302 once again, at block 1504, presents the target stimuli and, at block 1506, presents the foil stimuli. If no more captured response data is required, at block 1514, the facial response module 1310 creates a training set 1316 by labeling the captured response data, preferably comprising the response data to both the target stimuli and the foil stimuli.

At 1516, the machine learning module 1312 applies machine learning approaches to the training set 1316, and, at 1518, develops a computational response model 1318 by either creating a computational response model 1318 or refining an existing computation response model 1318.

In a further embodiment, the method 1500 can further include, at 1520, capturing, by the input sensing device 1304, unidentified facial response data to a stimulus from a separate human subject. The machine learning module 1312 then, at 1522, using machine learning techniques, employs the response model 1318 to the unidentified facial response data to determine whether the human subject's subliminal response was to subliminal target stimuli or foil stimuli. The machine learning module 1312 can also produce a normalized intensity measure of the unidentified facial response data. At 1524, the output module 1314 outputs the determination of whether the unidentified facial response data was subliminal target or foil stimuli, and the response intensity measure, to the output device 1320.

In further embodiments, optical sensors pointing, or directly attached to the skin of any body parts such as for example the wrist or forehead, in the form of a wrist watch, wrist band, hand band, clothing, footwear, glasses or steering wheel may be used. From these body areas, the system may also extract blood flow data for subliminal responses.

In still further embodiments, the system may be installed in robots and their variables (e.g., androids, humanoids) that interact with humans to enable the robots to detect subliminal responses on the face or other-body parts of humans whom the robots are interacting with. Thus, the robots equipped with transdermal optical imaging capacities read the humans' subliminal responses to enhance machine-human interaction.

Applicant recognized the substantial advantages of the system and method as described herein. As an example, the foregoing embodiments can detect subliminal responses on a human subject's face remotely, non-invasively, non-intrusively, and, in some cases, covertly. Additionally, the foregoing embodiments use a data driven approach, in addition to machine learning approaches, that allows the development of computational models to detect specific subliminal responses to specific subliminal stimuli with high-degree of accuracy. In addition, due in part to the forgoing embodiments that use a data driven approach, the computational response models 1318 can be based on a large sample of human subjects. Therefore, the response models 1318 can be applied to new, previously uncaptured, human subjects with high accuracy (so long as the new subjects are similar to the sample of subjects on whom the computational response models 1318 are based).

The foregoing system and method may be applied to a plurality of fields. In one embodiment the system may be installed in police stations and collect videos of a subject while being subliminally exposed to crucial crime-relevant vs irrelevant information to determine whether the subject is knowledgeable about a particular crime. In another embodiment, this system can be used in intelligence or governmental agencies for security clearance and related purposes. A further embodiment is at the border entry for detecting threats or smuggling, for example whether passengers are carrying explosives or illegal substances.

Further embodiments include marketing, advertising and sales, in particular, as subliminal responses can predict purchasing behavior and brand loyalty. In an embodiment, the system may collect videos of individuals while being exposed to a commercial advertisement, using a given product or browsing in a retail environment. The video may then be analyzed in real time to provide live user feedback on a plurality of aspects of the product or advertisement. Said embodiments may assist in identifying subliminal stimulation and responses required to induce a purchase decision in a consumer, as well as whether a product is positively or negatively received.

In still further embodiments, the system may be used as a tool in affective neuroscience. For example, the system may be coupled with a MRI, near infrared spectroscopy (NIRS) or EEG system to measure not only the neural activities associated with subjects' emotions but also subliminal facial response changes. Collected facial subliminal response data may be used either to provide additional and separating information regarding subjects' separate conscious and subconscious responses.

Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A computer-implemented method for detecting subliminal facial responses of a target human subject to subliminal stimuli, the method comprising:

receiving captured first facial response data approximately time-locked with a presentation of subliminal target stimuli to a plurality of human subjects;

receiving captured second facial response data approximately time-locked with a presentation of subliminal foil stimuli to the plurality of human subjects;

receiving captured unidentified facial response data to a subliminal stimulus from the target human subject;

determining a target probability measure that the unidentified facial response data of the target human subject is in response to the subliminal target stimuli using a machine learning model trained with a subliminal response training set, the subliminal response training set comprising the captured first facial response data and the captured second facial response data; and outputting the target probability measure.

2. The method of claim 1, further comprising determining a foil probability measure that the unidentified facial response data of the target human subject is in response to the subliminal foil stimuli, and outputting the foil probability measure.

3. The method of claim 1, further comprising determining an intensity measure for the unidentified facial response data of the target human subject in response to the subliminal target stimuli, and outputting the intensity measure.

4. The method of claim 1, wherein the subliminal target stimuli and the subliminal foil stimuli comprise visual stimuli.

5. The method of claim 1, wherein the subliminal target stimuli and the subliminal foil stimuli comprise auditory stimuli.

6. The method of claim 1, wherein the subliminal target stimuli and the subliminal foil stimuli are presented for less than approximately one second.

7. The method of claim 6, wherein the subliminal target stimuli and the subliminal foil stimuli are presented for less than approximately twenty milliseconds.

8. The method of claim 1, wherein the first facial response data, the second facial response data, and the unidentified facial response data are captured from predetermined regions of interest (ROIs) on the face of the subject, and wherein the response data is averaged for each of the ROIs.

9. The method of claim 1, wherein the first facial response data, the second facial response data, and the unidentified facial response data each comprise at least one of transdermal optical imaging data, facial expression data, thermal imaging data, and eye tracking data.

10. The method of claim 9, wherein the transdermal optical imaging data is acquired by determining, using a machine learning model trained with a hemoglobin concentration (HC) training set, bit values from a set of bitplanes in a captured image sequence that represent the HC changes of the human subject, the set of bitplanes being those that are determined to approximately maximize a signal-to-noise ratio (SNR), the HC training set comprising bit values from each bitplane of images captured from a set of subjects for which HC is known.

11. A system for detecting subliminal facial responses of a target human subject to subliminal stimuli, the system comprising one or more processors and a data storage device, the one or more processors configured to execute:

a facial response module to receive captured first facial response data from an input sensing device approximately time-locked with a presentation of subliminal target stimuli by a stimuli device to a plurality of human subjects, the facial response module further receiving captured second facial response data from the input sensing device approximately time-locked with a presentation of subliminal foil stimuli by the stimuli device to the plurality of human subjects, the facial response module further receiving captured unidentified facial response data from the input sensing device to a subliminal stimulus presented by the stimuli device from the target human subject;

a machine learning module to determine a target probability measure that the unidentified facial response data of the target human subject is in response to the subliminal target stimuli using a machine learning model trained with a subliminal response training set, the subliminal response training set comprising the captured first facial response data and the captured second facial response data; and an output module to output the target probability measure.

12. The system of claim 11, wherein the machine learning module further determines a foil probability measure that the unidentified facial response data of the target human subject is in response to the subliminal foil stimuli, and wherein the output module outputs the foil probability measure.

13. The system of claim 11, wherein the machine learning module further determines an intensity measure for the unidentified facial response data of the target human subject in response to the subliminal target stimuli, and wherein the output module outputs the intensity measure.

14. The system of claim 11, wherein the stimuli device presents the subliminal target stimuli and the subliminal foil stimuli as visual stimuli.

15. The system of claim 11, wherein the stimuli device presents the subliminal target stimuli and the subliminal foil stimuli as auditory stimuli.

16. The system of claim 11, wherein the stimuli device presents the subliminal target stimuli and the subliminal foil stimuli for less than approximately one second.

17. The system of claim 16, wherein the stimuli device presents the subliminal target stimuli and the subliminal foil stimuli for less than approximately twenty milliseconds.

18. The system of claim 11, wherein the first facial response data, the second facial response data, and the unidentified facial response data are captured by the input sensing device from predetermined regions of interest (ROIs) on the face of the subject, and wherein the facial response module or the machine learning module averages the response data for each of the ROIs.

19. The system of claim 11, wherein the first facial response data, the second facial response data, and the unidentified facial response data each comprise at least one of transdermal optical imaging data, facial expression data, thermal imaging data, and eye tracking data.

20. The system of claim 19, wherein the transdermal optical imaging data is acquired by determining, using a machine learning model trained with a hemoglobin concentration (HC) training set, bit values from a set of bitplanes in a captured image sequence that represent the HC changes of the human subject, the set of bitplanes being those that are determined to approximately maximize a signal-to-noise ratio (SNR), the HC training set comprising bit values from each bitplane of images captured from a set of subjects for which HC is known.

* * * * *